United States Patent
Lusser et al.

(10) Patent No.: US 7,323,690 B2
(45) Date of Patent: Jan. 29, 2008

(54) COMPACT SPECT RETROFIT FOR A CT SCANNER

(75) Inventors: Markus Lusser, Cary, IL (US); Michael Reitermann, Arlington Heights, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 37 days.

(21) Appl. No.: 11/387,529

(22) Filed: Mar. 23, 2006

(65) Prior Publication Data

US 2007/0221851 A1  Sep. 27, 2007

(51) Int. Cl.
*G01T 1/166* (2006.01)
(52) U.S. Cl. ............................................. 250/363.04
(58) Field of Classification Search .......... 250/363.08, 250/363.05, 363.04
See application file for complete search history.

(56) References Cited

U.S. PATENT DOCUMENTS

| | | | |
|---|---|---|---|
| 6,940,941 B2 * | 9/2005 | Gregerson et al. | 378/4 |
| 2001/0029334 A1 * | 10/2001 | Graumann et al. | 600/437 |
| 2004/0260171 A1 * | 12/2004 | Graumann | 600/411 |

* cited by examiner

*Primary Examiner*—Constantine Hannaher

(57) ABSTRACT

A compact SPECT imaging device generally includes a base assembly, a control tower assembly, a linkage assembly and a pair of detectors. The base assembly includes a plurality of fastening and/or anchoring assemblies such that the base assembly can be detachably fastenably secured between a gantry of an existing CT imaging device and a subject table. Preferably, the detectors of the compact SPECT imaging device are oriented with respect to one another at an angle of 90°. Preferably, the compact SPECT imaging device includes at least one input/output for communicatively connecting a peripheral device, such as a computer that is also connected to an existing CT imaging device.

17 Claims, 6 Drawing Sheets

PRIOR ART

COMPACT SPECT RETROFIT FOR A CT SCANNER

FIELD OF THE INVENTION

The instant invention relates generally nuclear medical imaging devices, and more specifically, to a compact SPECT nuclear imaging device that can be retrofitted to an existing CT nuclear imaging device such that both diagnostic modalities can be conducted in a single scanning session.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

In nuclear imaging, a patient is injected with or swallows a radioactive isotope which has an affinity for a particular organ, structure or tissue of the body. Gamma rays are then emitted from the body part of interest, are collimated by a collimator so that only gamma photons traveling in a direction perpendicular to the surface of a detector head are allowed to impinge on the detector head, and are detected by a gamma camera apparatus including the detector head, which forms an image of the organ based on the detected concentration and distribution of the radioactive isotope within the body part of interest. Nuclear images may be obtained using Single Photon Emission Computed Tomography (SPECT). SPECT produces multiple image "slices," each representing a different plane in a three-dimensional region, such that when the slices are considered collectively, a three-dimensional image of the region may be studied.

SPECT imaging is performed by using a gamma camera to acquire multiple images (also called projections) from multiple angles. A computer can then be used to apply a tomographic reconstruction algorithm to the multiple projections, yielding a 3D dataset.

To acquire SPECT images the gamma camera is rotated around the patient. Projections are acquired at defined points during the rotation, typically every 3-6 degrees. In most cases, a full 360 degree rotation is used to obtain an optimal reconstruction.

Multi-headed gamma cameras can provide accelerated acquisition. For example, a dual headed camera can be used with heads spaced 180 degrees apart, allowing 2 projections to be acquired simultaneously, with each head only requiring 180 degrees of rotation. Triple-head cameras with 120 degree spacing are also used.

Another known tomography system is computed axial tomography (CAT, or now also referred to as CT, XCT, or x-ray CT). In CT, an external x-ray source is caused to be passed around a patient. Detectors around the patient then respond to the x-ray transmission through the patient to produce an image of the area of study. Unlike SPECT, which is an emission tomography technique because it relies on detecting radiation emitted from inside the patient, CT is a transmission tomography technique which utilizes a radiation source external to the patient. CT provides images of the internal structures of the body, such as the bones, whereas SPECT provides images of the functional aspects of the body, usually corresponding to an internal organ or tissue.

A CT scanner uses a similar mechanical setup as the SPECT scanner. However, unlike SPECT, a CT scanner requires detectors mounted opposite an x-ray source. In third-generation computed tomography systems, the CT detectors and x-ray source are mounted on diametrically opposite sides of a gantry which is rotated around the patient as the patient traverses the tunnel of the gantry.

The x-ray source of a CT imaging device emits a fan-shaped beam of x-rays which pass through the patient and are received by an array of detectors. As the x-rays pass through the patient, they are attenuated as a function of the densities of objects in their path. The output signal generated by each detector is representative of the electron densities of all objects between the x-ray source and the detector.

The CT detectors can utilize scintillator crystals which are sensitive to the energy level of the x-rays. Multiple light pulses produced by each scintillator crystal as it interacts with the x-rays are integrated to produce an output signal which is related to the number of the x-rays sensed by the scintillator crystal. The individual output signals are then collectively processed to generate a CT image. Other detectors can be used in CT tomographs. For example, a solid state silicon diode can be used to detect the low energy x-rays directly.

CT imaging is generally suited for providing anatomical and structural information, whereas SPECT is more adept for studying function and activity of tissue and organs. Consequently, it is particularly useful in certain studies such oncological and cardiology studies to use SPECT imaging for diagnostic purposes, and to align or register the nuclear image with a medical image from another modality such as CT, which offers better anatomical information. Such a fused image, for example, enables clinicians to determine the anatomical position of a lesion displayed by the nuclear image more accurately and the organs and structures that are affected can be ascertained with a higher degree of accuracy and confidence.

Hybrid imaging devices, which combine the functional sensitivity of SPECT with the anatomical detail of diagnostic multi-slice CT in a single; integral imaging device, are known. However, such integrated devices are costly and impractical for diagnostic service providers that already possess stand alone-type CT imaging devices. Indeed, it may not be economically feasible for a diagnostic service provider to purchase a new, integrated hybrid device when such individual already possesses a stand alone-type CT imaging device. Additionally, in many instances, clinicians may have already constructed special buildings or rooms with which to house their existing stand alone-type CT imaging device such that the purchase of a new hybrid device may require the demolition and/or construction of a new building or room—which can be undesirable and/or cost prohibitive. Consequently, there is a need for a compact SPECT imaging device that can be retrofitted with an existing stand alone-type CT imaging device to thereby form a hybrid device.

SUMMARY OF THE INVENTION

A compact SPECT imaging device according to the instant invention that can be retrofitted with an existing CT imaging device generally comprises a base assembly, a control tower assembly, a linkage assembly and at least one detector. The base assembly comprises a plurality of fastening assemblies for detachably fastenably securing and/or anchoring the compact SPECT imaging device in a desired position between the gantry of an existing stand alone-type CT imaging device and a subject table. In one embodiment, the compact SPECT imaging device comprises a pair of detectors disposed with respect to one another at an angle of 90°. In another embodiment, the compact SPECT imaging device further comprises at least one electrical input/output for electrically connecting a peripheral device. In still yet another embodiment, the peripheral device is a computer. In some embodiments, the computer is electrically connected to an existing CT imaging device. In one embodiment, the electrical input/output is a wireless connection.

In some embodiments of the invention, a compact SPECT imaging device is associated with an existing stand alone-type CT imaging device comprising a gantry and a subject table and the compact SPECT imaging device is detachably fastenably securable between the gantry and the subject table of the existing CT imaging device. In one embodiment, the compact SPECT imaging device comprises a base assembly having a plurality of fastening assemblies, a control tower assembly, a linkage assembly, and preferably, a pair of detectors that are disposed with respect to one another at an angle of 90°. In another embodiment, the base assembly is detachably fastenably securable below the subject table. In some embodiments, the control tower comprises a motor that is mechanically connected to the linkage assembly and the linkage assembly is mechanically connected to the detectors such that the motors can rotate the detectors about an axis. In some embodiments, the compact imaging device and/or the existing stand alone-type CT imaging device comprises an alignment assembly for properly positioning the compact SPECT imaging device with respect to the existing CT imaging device and/or the table at a predetermined position. In some embodiments, the compact SPECT imaging device and the CT imaging device are electrically connected to a common computer. In some embodiments, the compact SPECT imaging device includes an onboard power source such as a rechargeable battery.

BRIEF DESCRIPTION OF THE DRAWINGS

An exemplary embodiment of the instant invention will now be more fully described in the detailed description and accompanying figures that follow in which.

DETAILED DESCRIPTION OF THE PREFERRED EMBODIMENTS

At the outset, it should be appreciated that the term/phrase "retrofit" and related terms/phrases is intended to refer to the fact that the present invention is configured to be combined, used in combination with, and/or mated with an existing stand alone-type CT imaging device. Additionally, the terms/phrases "open," "open architecture" and related terms are intended to refer to generally non-annular imaging devices of the type that do not dispose a subject in and out of an orifice or tunnel and/or that do not wholly surround a subject.

Figure 1:
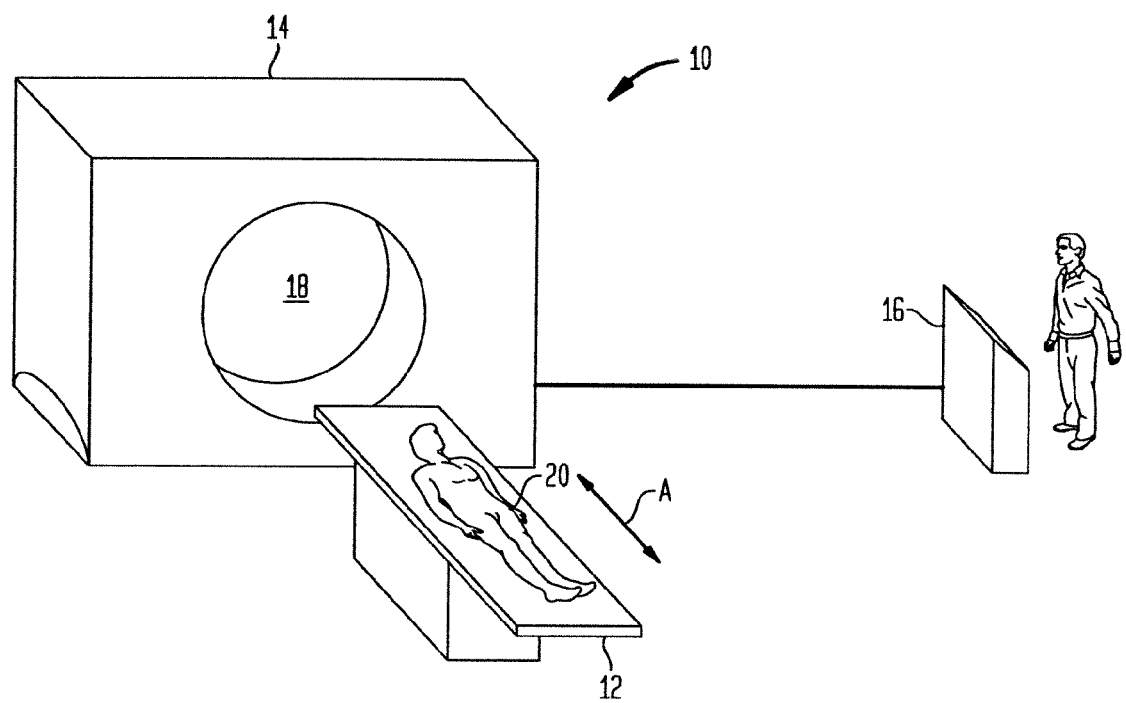
FIG. 1 is a perspective view of a known stand alone-type CT imaging device.

Referring now to the Figures, FIG. 1 illustrates an example of a known stand alone-type CT imaging device 10. Known stand alone-type CT imaging device 10 generally comprises table 12, gantry 14 and operator station 16. Table 12 is generally provided for supporting a subject to be examined thereon and can be inserted into and out of tunnel/orifice 18 of gantry 14 in the directions of arrow A. Gantry 14, which forms an annulus, is provided for supporting and rotating one or more radiation sources and detectors about a subject 20 to be examined such that image data regarding the subject can be collected. Operator station 16, which can include a computer, is provided for rendering three-dimensional images using the collected image data. Operator station 16 can be located in a room separate from gantry 14. Such types of stand alone CT imaging devices are typically substantial in size and weight, have large footprints and are immobile. Often, rooms and/or buildings must be specifically constructed and/or designed in order to house such stand-alone CT imaging devices.

Figure 2:
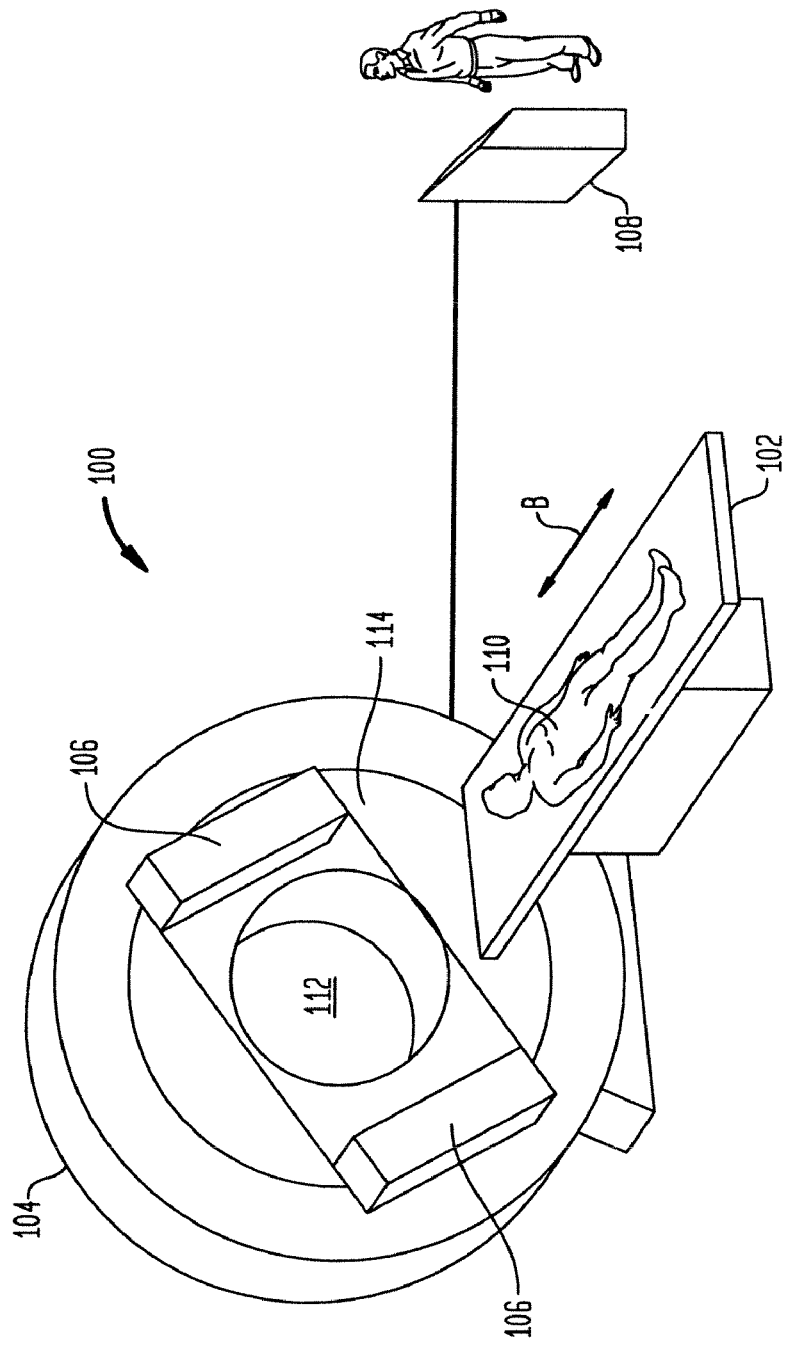
FIG. 2 is a perspective view of a known stand alone-type SPECT imaging device.

Referring now to FIG. 2, an example of a known stand alone-type SPECT imaging device 100 is seen as broadly comprising table 102, gantry 104, detectors 106 and operator station 108. Table 102 is generally provided for supporting a subject 110 thereon and is movable in and out of tunnel/orifice 112. Gantry 104 forms an annulus and is provided for supporting and rotating detectors 106 about subject 110. A rotational drive assembly including a rotating drum 114 and a drive motor and linkage assembly (not shown) is provided for rotating the drum and detectors about the subject. Generally, each of the detectors 110 comprises a scintillation crystal (not shown) that converts radiation that is received into flashes or scintillations of light, which are received by photomultiplier tubes (PMT's) (not shown) such that image data regarding the subject may be obtained. Operator station 108 can comprise a computer (not shown) that is used to prepare three dimensional images of the subject from the image data that is collected. Such types of stand alone-type SPECT imaging devices are typically substantial in size and weight, have large footprints and are immobile. Much like stand alone-type CT imaging devices, these devices also typically require that a special building or room be constructed to accommodate the device.

Figure 3:
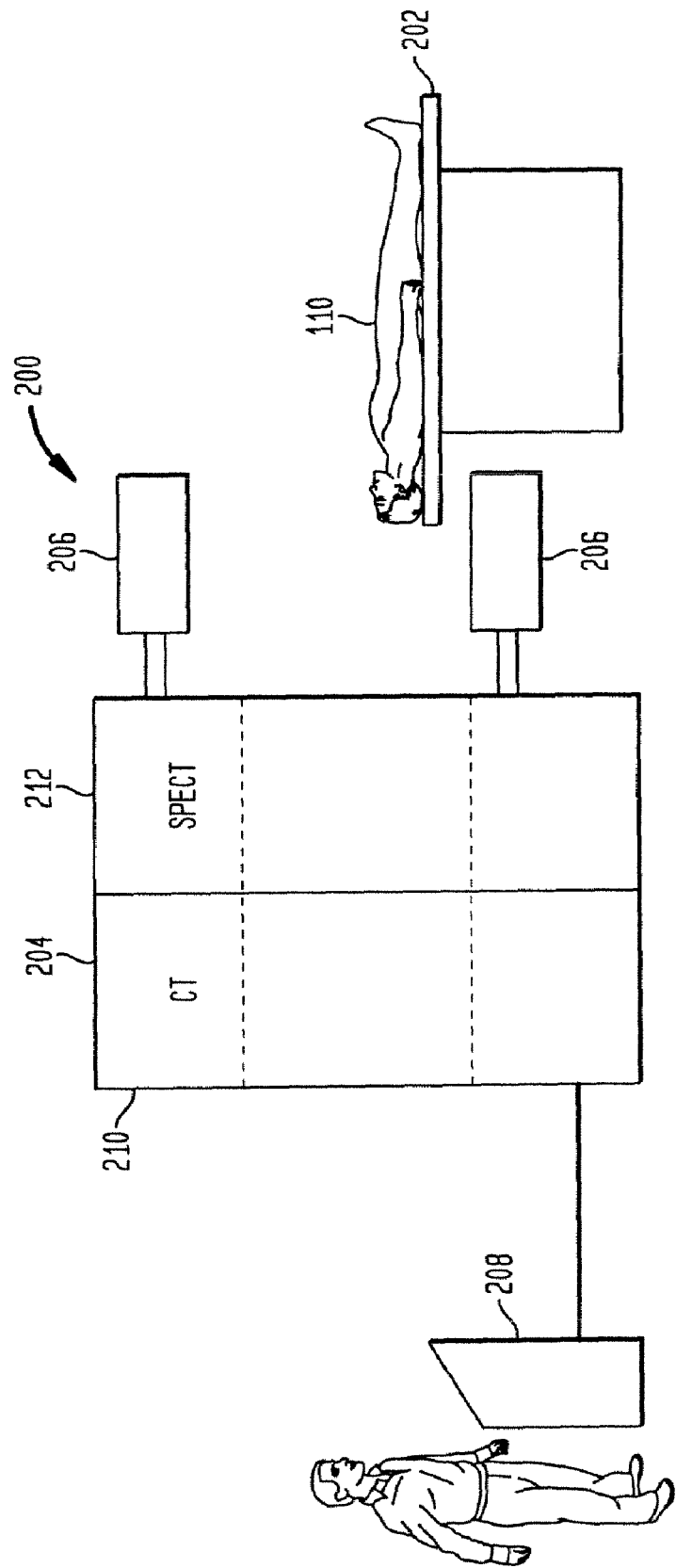
FIG. 3 is a perspective illustration of a known integrated CT/SPECT imaging device.

Referring now to FIG. 3, an example of a known integral SPECT/CT imaging device 200 is illustrated as broadly comprising table 202, gantry housing 204, scintillating detectors 206 and operator station 208. Table 202 is generally provided for supporting a subject 110 thereon. Gantry housing 204 forms an annulus, which supports internal radiation source(s) and detector(s) therefor (not shown) for performing CT analyses on side 210 of housing 204 and supports a pair of external scintillating detectors 206 for performing SPECT analyses (which typically include collimators) on side 212 of housing 204. Operator station 208, which can comprise a computer, is provided for controlling the CT and/or SPECT analyses and also renders three dimensional images of a subject that is scanned. These devices are also typically substantial in size and weight, have large footprints and are generally immobile.

Figure 4:
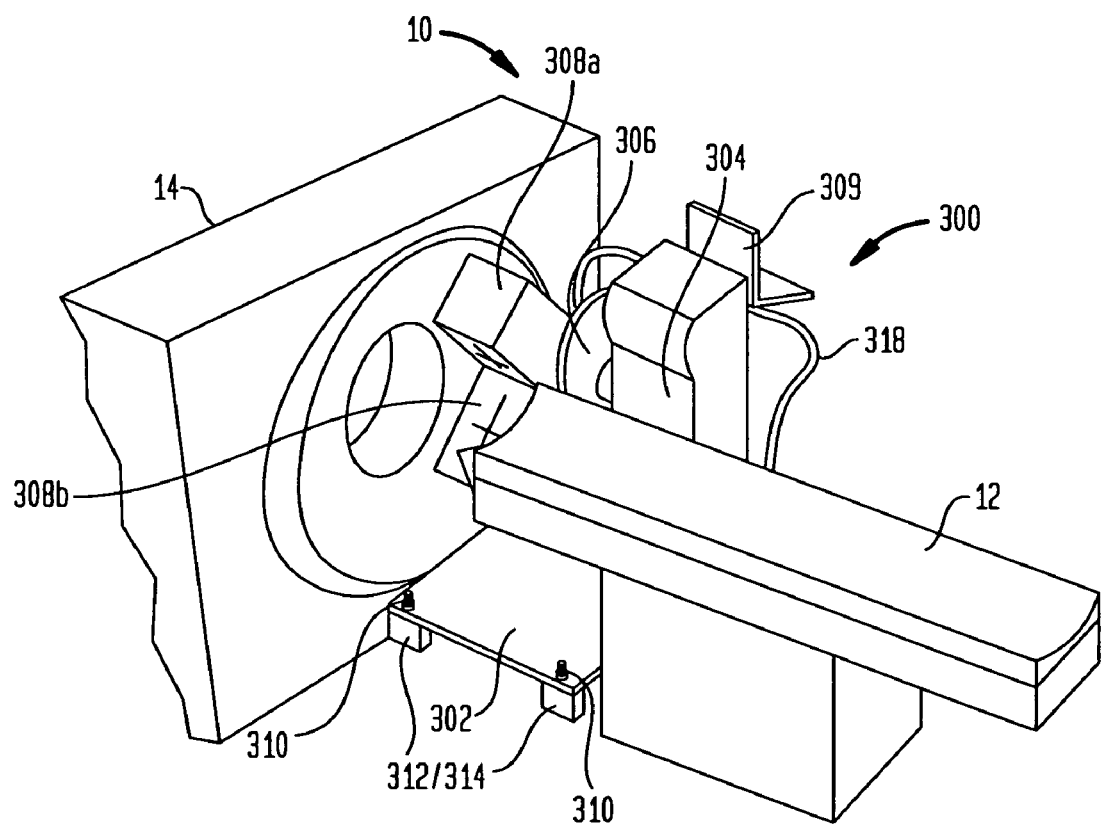
FIG. 4 is a perspective view of an existing stand alone-type CT imaging device retrofitted with a compact SPECT imaging device according to the instant invention.

Referring now to FIG. 4, according to the instant invention, known stand-alone CT imaging device 10 is illustrated as being retrofitted with compact SPECT imaging device 300. More specifically, compact SPECT imaging device 300 is illustrated as being positioned between subject table 12 and annular gantry 14 of stand alone-type CT imaging device 10. Compact SPECT imaging device 300 generally comprises base assembly 302, control tower assembly 304, linkage assembly 306, detectors 308a, 308b and operator station 309, which alternatively, may be located in a separate room and in electronic communication with control tower assembly 304.

Figure 5:
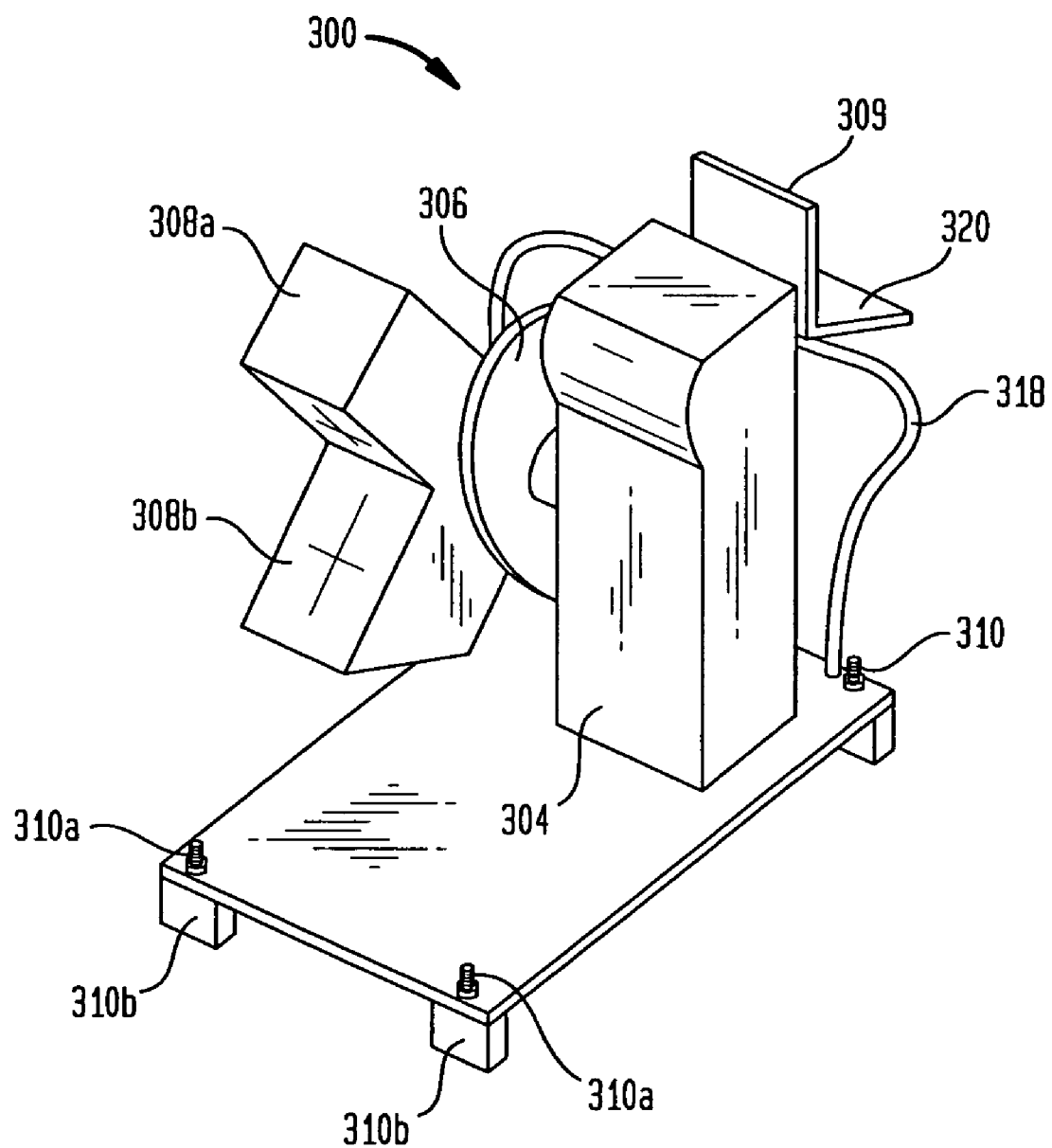
FIG. 5 is a perspective view of a compact SPECT imaging device according to one embodiment of the instant invention, which for illustrative purposes, is shown as being separated from an existing stand alone-type CT imaging device.
Figure 6:
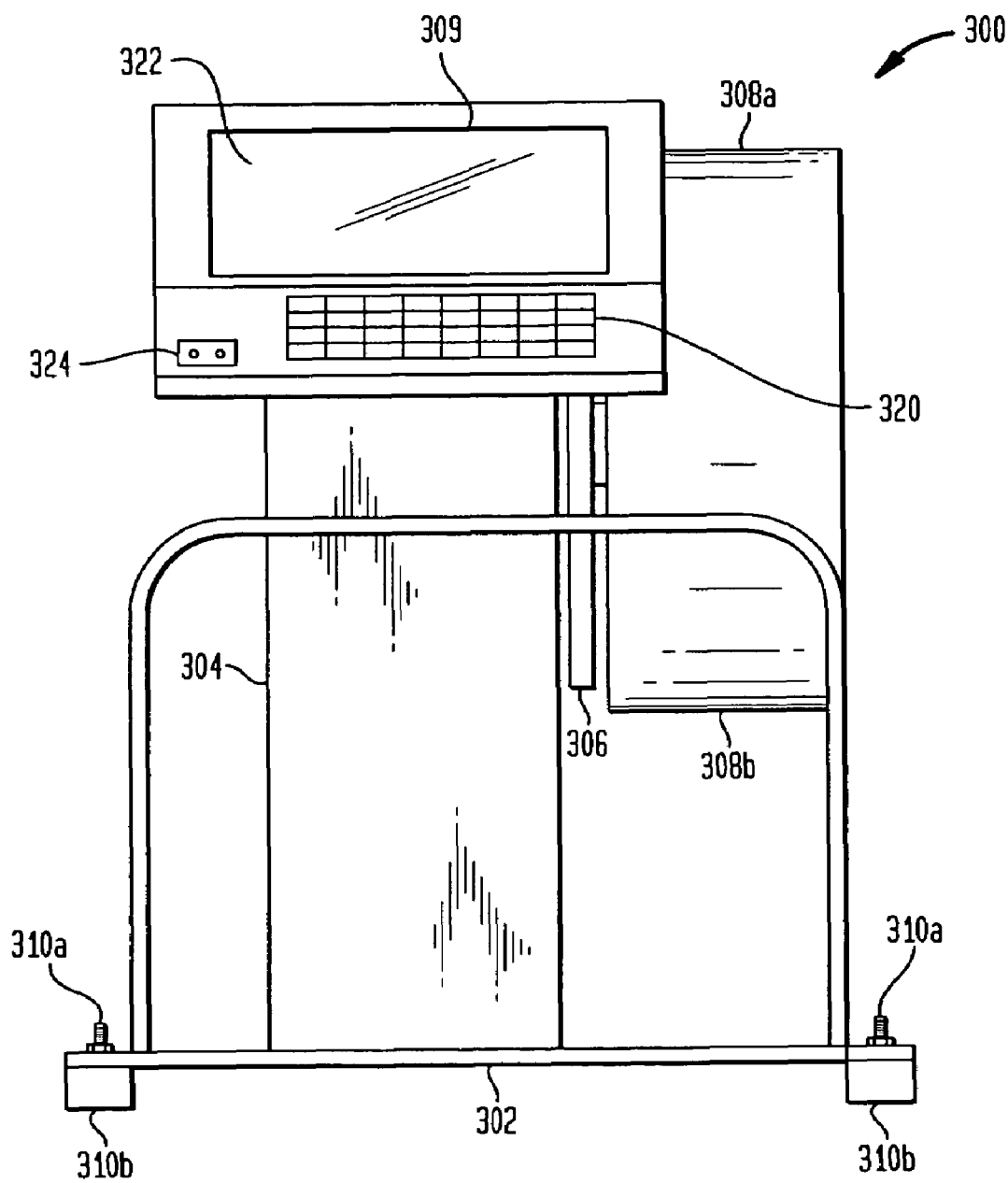
FIG. 6 is a rear plan view of a compact SPECT imaging device according to one embodiment of the present invention.

As illustrated more clearly in FIGS. 5-6, base assembly 302 is sized and shaped for positioning between annular gantry 14 and subject table 12 and comprises a plurality of fastening assemblies for 310 for detachably fastening/anchoring the device in a desired position. Fastening assemblies 310 can comprise nuts and bolts (310a), which secure the compact SPECT imaging device to the existing CT imaging device and the subject table. Alternatively, compact SPECT imaging device can be detachably fastenably secured in a desired position by fasteners that are securable to the floor (310a). Additionally, or in the alternative, the fastening assemblies 310 can comprise a plurality of pads or shoes (e.g. rubber pads or feet 310b), which act in cooperation with fastening assemblies 310a or can act alone to positionally secure the compact SPECT imaging device in a desired location using only the weight of the device. For purposes of providing stability to the compact SPECT imaging device 300, fastening assemblies 310 can be disposed at the corners of the base assembly, which is illustrated as being generally rectangular, planar and having a relatively low ground clearance.

Base assembly 302, gantry 14 and/or subject table 12 can be configured to comprise alignment assemblies 312, 314 for properly disposing and/or locking the SPECT imaging device 300 at a predetermined position prior to performing a scanning procedure. Alignment assemblies 312, 314 can be fastened to one or more of the existing CT imaging device 10, subject table 12 and/or SPECT imaging device 300 to properly align such structures relative to one another. Base assembly 302 can also be configured to comprise a power cord that can be plugged into a central power source, such as a wall outlet. Such power cord may be retractable, if desired. In addition, or in the alternative, base assembly 302 can be configured to comprise an onboard power source, such as a rechargeable battery. Such onboard power source can allow the compact SPECT imaging device to be used without having to connect the device to a central power source. This is advantageous because existing CT imaging devices may not comprise auxiliary power outlets for receiving a power cord therein and/or it may not be desirable to extend a power cord across a room to a power outlet. Base assembly 302 is further provided for securing control tower assembly 304.

Control tower assembly 304 is generally provided for serving as a support for detectors 308a, 308b, which are connected thereto by linkage assembly 306. Control tower assembly 304 houses motion control devices (not shown), for example, motors, which work in conjunction with linkage assembly 306 to cause movement of the detectors. Detector movements can include, but are not limited to: up, down, left or right, inward and outward, and rotation about one or more axes. Control tower assembly 304 may also be configured to comprise a computer 320, which can be a laptop type computer, a display 322 and/or communications link 324 for connecting the compact SPECT imaging device 300 with existing CT imaging device 10, for example, for sending/receiving commands from one device to the other, for displaying image information, or for registering SPECT image data with CT image data, etc. Communications link 324 can be a wired or wireless (e.g., RF, microwave, Bluetooth, light, infrared, etc.) connection.

In the embodiment illustrated, detectors 308a, 308b are connected and disposed with respect to one another at an angle of approximately 90° to thereby provide an open-type architecture. Detectors 308a, 308b can be of a type generally known in the art and can comprise collimators and scintillating crystals, which are placed between the subject table and the gamma ray camera. In general, the collimators help to eliminate substantially all photons but those photons traveling in a desired direction and the scintillating crystals produce a flash or light event when a gamma photon collides therewith and is absorbed by the crystal. Detectors 308a, 308b are generally configured for being rotated with respect to a subject disposed on subject table 12 and receiving gamma photons that emanate from the subject. It should be appreciated by those having ordinary skill in the art that while the illustrated embodiment preferably discloses a pair of detectors 308a, 308b as being connected to one another and oriented with respect to one another at an angle of 90°, one or more detectors may be utilized and/or a number of detectors may be independently movable with respect to one another such that the angles of orientation therebetween may be modified.

Finally, as previously noted, computer 320 of the compact SPECT imaging device can be utilized for outputting images data and registering SPECT image data with CT image data. Computer 320 generally comprises a central processing unit (CPU) in communication with the existing CT imaging device. Computer 320 can include various input/output (I/O) device(s) communicating over a bus, including, for example, a keyboard, a mouse, a video monitor, a printer, and/or other devices. In some embodiments, the CPU can communicate with a computer readable medium (e.g., conventional volatile or non-volatile data storage devices) (hereinafter "memory") over the bus. The memory can include, e.g., data and software for performing a plurality of various imaging operations. Generally, the system geometries of the two devices are known; that is, the offset between the Field of View (FOV) of the compact SPECT imaging device and that of the existing CT imaging device are known.

In a first method of registering images, the FOV of the SPECT system can be positioned using a Patient Positioning Monitor (PPM) in a known manner that is similar to that which is currently done using a stand-alone SPECT system. Then, the extent of the CT scan can be matched to cover the FOV of the SPECT scan. In a second method, the extent of the CT scan can be specified to be a sub-portion of that covered in the PPM. In various embodiments, any desired method of specifying can be employed, such as, by way of example, using marker lines on the PPM. In this manner, lines or the like can be used to specify a sub-portion of the PPM image in which to acquire CT image data. Among other things, this can help to limit the amount of x-ray dose delivered to the patient by limiting the extent of the scan (e.g., in the axial direction).

In some embodiments, the only positioning information provided by the existing CT imaging device is the use of laser markers or physical landmarks. In some examples, if this information is not sufficient, then the system can be configured to allow the operator to acquire a CT Tomogram to use in conjunction with the PPM information. In some embodiments, this can be performed routinely, or, alternatively, it can be included optionally, as needed. Accordingly, a third positioning method is contemplated as described below.

In the third method, the PPM can be used in conjunction with a Tomogram (e.g., a CT Tomogram) by displaying PPM information along with the Tomogram image. In some examples, a simplified method of doing this can be to display the extent of the PPM FOV as an annotation overlaid on the Tomogram image. For example, in some embodiments, the system can be configured to enable a user to simply draw a box (such as, e.g., using any computer software GUI methodologies similar to that of other software applications) on the Tomogram indicating the position of the SPECT FOV. In some more sophisticated methods, the PPM image is stored and that image is overlaid (e.g., using alpha blending or other techniques) with the Tomogram. In some embodiments, the user can then set the extent of the CT scan using the registered data from both modalities.

In some embodiments, the CT FOVs determined by the SPECT PPM images are treated as initial settings for the extent of the CT scan. In the preferred embodiments, however, the system is configured to allow the user to modify these extents to further refine the area to perform the CT scan. In these cases, it is useful to display the original PPM FOV even when the user has modified the scan extent (e.g., this can be helpful to enable the user to keep track and avoid losing this "landmark" information).

In some embodiments, the various methods described herein may be implemented via one or more computer program products for use with computer 320. This implementation may, for example, include a series of computer instructions fixed on a computer readable medium (e.g., a diskette, a CD-ROM, ROM or the like) or transmittable to a computer system via and interface device, such as a modem or the like. The medium may be substantially tangible (e.g., communication lines) and/or substantially intangible (e.g., wireless media using microwave, light, infrared, etc.). The computer instructions can be written in various programming languages and/or can be stored in memory device(s), such as semiconductor devices (e.g., chips or circuits), magnetic devices, optical devices and/or other memory devices. In the various embodiments, the transmission may use any appropriate communications technology.

While illustrative embodiments of the invention have been described herein, the present invention is not limited to the various preferred embodiments described herein, but includes any and all embodiments having equivalent elements, modifications, omissions, combinations (for example, various aspects in different embodiments can be combined together when appropriate in various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

What is claimed is:

1. In combination with a stationary standalone CT imaging device comprising a gantry and a subject table, a compact SPECT imaging device retrofittable with said standalone CT imaging device, said compact SPECT imaging device being detachably and fastenably secured between said gantry and said subject table, wherein said compact SPECT imaging device comprises a base assembly for coupling and supporting, a control tower assembly, a linkage assembly and a pair of detectors disposed with respect to one another at an angle of 90, said base assembly being adaptable to being coupled to at least one of a floor and said CT imaging device, said SPECT Imaging device and a table.

2. The combination of claim 1 wherein said base assembly comprises a plurality of fastening assemblies.

3. The combination of claim 1 wherein said base assembly is positionable below said subject table.

4. The combination of claim 1 wherein said control tower comprises a motor, said motor mechanically connected to said linkage assembly, said linkage assembly mechanically connected to said detectors, said motor configured for rotating said detectors about an axis.

5. The compact SPECT imaging device of claim 1 further comprising a plurality of detectors configured in an open-architecture type configuration.

6. The compact SPECT imaging device of claim 1 comprising an alignment assembly, said alignment assembly positioning said compact SPECT imaging device with respect to said existing CT imaging device and said table at a predetermined position.

7. The compact SPECT imaging device of claim 1 comprising at least one input/output assembly, said input/output assembly providing a connection between said compact SPECT imaging device to a peripheral device.

8. The compact SPECT imaging device of claim 7 wherein said connection is wired.

9. The compact SPECT imaging device of claim 7 wherein said connection is wireless.

10. The compact SPECT imaging device of claim 7 wherein said peripheral device is a computer.

11. The compact SPECT imaging device of claim 10 wherein said compact SPECT imaging device and said existing CT device are electrically connected to said computer.

12. The compact SPECT imaging device of claim 1 comprising an onboard power source.

13. The compact SPECT imaging device of claim 12 wherein said power source is rechargeable.

14. A compact SPECT imaging device comprising:
a base assembly, a control tower assembly, a linkage assembly and a pair of detectors disposed with respect to one another at an angle of substantially 90°, said base assembly comprising a plurality of fastening assemblies, said base assembly being detachably and fastenably secured between a gantry of a standalone CT imaging device and a subject table, a base assembly for coupling and supporting, a control tower assembly, a linkage assembly and a pair of detectors disposed with respect to one another at an angle of 90, said base assembly being adaptable to being coupled to at least one of a floor and a CT imaging device and said SPECT Imaging device and a table, said compact SPECT imaging device further comprising at least one electrical input/output interface for electrically connecting said SPECT imaging device to a peripheral device.

15. The compact SPECT device of claim 14 wherein said peripheral device is a computer.

16. The compact SPECT imaging device of claim 15 wherein said computer is electrically connected to said existing CT imaging device.

17. The compact SPECT device of claim 14 wherein said electrical input/output interface is wireless.

* * * * *